US009179051B1

(12) United States Patent
Stoudt

(10) Patent No.: US 9,179,051 B1
(45) Date of Patent: Nov. 3, 2015

(54) VOICE-ACTIVATED HANDS-FREE CAMERA HOLDER SYSTEMS

(71) Applicant: Clara Stoudt, Kutztown, PA (US)

(72) Inventor: Clara Stoudt, Kutztown, PA (US)

( * ) Notice: Subject to any disclaimer, the term of this patent is extended or adjusted under 35 U.S.C. 154(b) by 0 days.

(21) Appl. No.: 14/293,628

(22) Filed: Jun. 2, 2014

Related U.S. Application Data

(60) Provisional application No. 61/834,714, filed on Jun. 13, 2013.

(51) Int. Cl.

| | |
|---|---|
| ***H04N 9/47*** | (2006.01) |
| ***H04N 7/18*** | (2006.01) |
| ***G03B 29/00*** | (2006.01) |
| ***G03B 41/00*** | (2006.01) |
| ***A61B 1/04*** | (2006.01) |
| ***A61F 5/28*** | (2006.01) |
| ***H04N 5/225*** | (2006.01) |

(52) U.S. Cl.
CPC .................................. *H04N 5/2252* (2013.01)

(58) Field of Classification Search
CPC .... A61B 19/2203; A61B 19/56; A61B 19/26; A61B 19/5225; A61B 19/5244; A61B 2017/00203; A61B 1/04; H04N 5/2252; H04N 9/47; H04N 7/18; G03B 29/00; G03B 41/00; A61F 5/28
USPC .......................... 348/373, 65–78; 396/14–18; 128/95.1–126.1
See application file for complete search history.

(56) References Cited

U.S. PATENT DOCUMENTS

| | | | | |
|---|---|---|---|---|
| 6,224,542 | B1 | 5/2001 | Chang | |
| 6,591,239 | B1 | 7/2003 | McCall | |
| 6,858,003 | B2 | 2/2005 | Evans | |
| 7,520,006 | B2 * | 4/2009 | Menkedick et al. | 5/618 |
| 8,286,282 | B2 * | 10/2012 | Kummer et al. | 5/615 |
| 8,499,379 | B2 * | 8/2013 | Ota et al. | 5/81.1 R |
| 8,875,585 | B2 * | 11/2014 | McCollum | 73/788 |
| 2002/0169512 | A1 * | 11/2002 | Stewart | 700/100 |
| 2005/0096502 | A1 * | 5/2005 | Khalili | 600/106 |
| 2007/0185376 | A1 * | 8/2007 | Wilson et al. | 600/102 |
| 2008/0078030 | A1 * | 4/2008 | Lee et al. | 5/616 |
| 2009/0036902 | A1 * | 2/2009 | DiMaio et al. | 606/130 |
| 2009/0248036 | A1 * | 10/2009 | Hoffman et al. | 606/130 |
| 2010/0268383 | A1 * | 10/2010 | Wang et al. | 700/248 |
| 2011/0146676 | A1 * | 6/2011 | Dallam et al. | 128/203.12 |
| 2011/0152882 | A1 * | 6/2011 | Wenderow et al. | 606/130 |
| 2011/0261180 | A1 * | 10/2011 | Simon et al. | 348/77 |
| 2011/0277775 | A1 * | 11/2011 | Holop et al. | 128/849 |
| 2012/0071892 | A1 * | 3/2012 | Itkowitz et al. | 606/130 |
| 2012/0154564 | A1 * | 6/2012 | Hoffman et al. | 348/65 |
| 2013/0211421 | A1 * | 8/2013 | Abovitz et al. | 606/130 |
| 2013/0307955 | A1 * | 11/2013 | Deitz et al. | 348/77 |
| 2013/0345718 | A1 * | 12/2013 | Crawford et al. | 606/130 |
| 2014/0005484 | A1 * | 1/2014 | Charles | 600/201 |
| 2014/0257330 | A1 * | 9/2014 | Choi et al. | 606/130 |
| 2014/0343416 | A1 * | 11/2014 | Panescu et al. | 600/431 |
| 2015/0057675 | A1 * | 2/2015 | Akeel et al. | 606/130 |
| 2015/0100066 | A1 * | 4/2015 | Kostrzewski et al. | 606/130 |

* cited by examiner

*Primary Examiner* — Chia-Wei A Chen
(74) *Attorney, Agent, or Firm* — RG Patent Consulting, LLC; Rachel Gilboy

(57) ABSTRACT

A voice-activated hands-free camera holder system is removably-installable to a patient operating station for adjustably-positioning a micro-camera via a plurality of verbal commands to assist a medical provider, such as a surgeon, during a surgical procedure. The voice-activated hands-free camera holder system includes a voice-activation assembly and a manual controller unit enabling the user to manipulate the micro-camera such that both hands of the user remain free for use during the procedure while providing the user with an ideal vantage angle for observation.

20 Claims, 5 Drawing Sheets

100 110 150 Voice Command 185 140 160 135 132 130 125 116 112 114 118 105 120

VOICE-ACTIVATED HANDS-FREE CAMERA HOLDER SYSTEMS

CROSS-REFERENCE TO RELATED APPLICATION

The present application is related to and claims priority from prior provisional application Ser. No. 61/834,714, filed Jun. 13, 2013 which application is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

The following includes information that may be useful in understanding the present invention(s). It is not an admission that any of the information provided herein is prior art, or material, to the presently described or claimed inventions, or that any publication or document that is specifically or implicitly referenced is prior art.

BACKGROUND OF THE INVENTION

1. Field of the Invention

The present invention relates generally to the field of video camera retaining devices and more specifically relates to a voice-activated hands-free video camera holding system for use during a surgical procedure.

2. Description of the Related Art

Surgeries performed modernly may be very complex. During laparoscopic surgery, a surgeon may be partially distracted by having to hold a camera to collect images of the operation. Yet, having a second person present solely to collect footage may be a waste of that person's time and resources.

Many cameras and camera retaining devices exist today which may allow a user to manually manipulate the camera holding device to achieve a preferred vantage point. However, the user must continuously manipulate the device using his or her hands in order to change vantage points. A more suitable solution that enables the user to manipulate the vantage angle in a hands-free manner is needed.

Various attempts have been made to solve the above-mentioned problems such as those found in U.S. Pat. No. 6,224,542 to William H. L. Chang, U.S. Pat. No. 6,591,239 to David F. McCall, and U.S. Pat. No. 6,858,003 to Philip C. Evans. This art is representative of voice activated video camera systems for use during medical procedures. None of the above inventions and patents, taken either singly or in combination, is seen to describe the invention as claimed.

Ideally, a voice-activated hands-free camera holder system should provide a hands-free solution to allow a surgeon to perform a procedure and adjust a zoom function and a camera angle of a camera while freely using both hands during the procedure, and, yet would operate reliably and be manufactured at a modest expense. Thus, a need exists for a reliable voice-activated hands-free camera holder system to avoid the above-mentioned problems.

BRIEF SUMMARY OF THE INVENTION

In view of the foregoing disadvantages inherent in the known video camera device retaining art, the present invention provides a novel voice-activated hands-free camera holder system. The general purpose of the present invention, which will be described subsequently in greater detail, is to provide a camera retaining apparatus that is removably-installable to a patient operating station for adjustably-positioning a micro-camera via a plurality of verbal commands to assist a medical provider, such as a surgeon, during a surgical procedure.

A voice-activated hands-free camera holder system (also known as "Clara Cam") may enable a doctor or surgeon to take hands-free camera footage during laparoscopic surgery. It improves a surgeon's ability to focus entirely on the task at hand. Further, it eliminates the need to have a second person present simply to operate a camera. It offers both voice activation and manual control options. The device may adjust and extends to various lengths and angles for inclusive, efficient use. The present invention may comprise a clamp for securing the device to an operating table.

A preferred embodiment of the present invention is disclosed herein comprising a voice-activated hands-free camera holder system which may comprise a supporting bar preferably manufactured of sterilized stainless steel to withstand a sterilization process, a voice-activation assembly comprising a voice-activation housing, a voice-activation processor, a microphone, a power source, an adjustable arm manufactured of sterilized stainless steel to withstand the sterilization process, a manual controller unit, and an extendable wand manufactured of sterilized stainless steel to withstand the sterilization process.

The extendable wand may comprise a camera-housing for retaining a micro-camera, a plurality of telescopic-coils which enable the extendable wand to extend and retract. It should be noted that the supporting bar, the voice-activation assembly, the adjustable arm, the manual controller unit, and the extendable wand comprises in functional combination the voice-activated hands-free camera holder system.

The supporting bar may generally comprise a rectangular member having a proximal end and a distal end. The distal end of the rectangular member may comprise a clamp. Preferably, the clamp may comprise a C-clamp (although any suitable clamp known in the art may be employed). The clamp is useful for non-movably attaching the supporting bar to a rail of a patient operating station. The clamp may further enable the supporting bar to adjust vertically approximately 6-8" for allowing the user to adjust the supporting bar to a user-preferred height. The proximal end of the rectangular member may comprise a voice-activation assembly connecting point for connecting the voice-activation housing of the voice-activation assembly to the supporting bar.

The voice-activation housing, the voice-activation processor, the microphone, and the power source comprise in functional combination the voice-activation assembly. The voice-activation housing may generally comprise a box-like enclosure having a first-side, a second-side, a top-side, and a bottom-side. The voice-activation processor, the microphone, and the power source may be fixedly mounted within the voice-activation housing. The voice-activation processor, the microphone, and the power source may be in electrical communication. The voice-activation processor may operate the voice-activation assembly when activated and verbally manipulated by a user. The voice-activation assembly may be powered by the power source. In the preferred embodiment, the power source comprises a power cable connectable to at least one external power supplier. In other embodiments, the power source may alternatively comprise at least one battery that is either rechargeable or non-rechargeable.

The voice-activation assembly connecting point may be rotatably-connected to the first-side of the voice-activation housing via a ball-and-socket joint. The top-side of the voice-activation housing may comprise the microphone which may include an acoustic-to-electric transducer useful for causing the voice-activation assembly to be verbally manipulated by the user. The adjustable arm may comprise an elongated flexible member having a first-end and a second-end. The second-side of the voice-activation housing may comprise an adjustable arm opening for fixedly retaining the first-end of the adjustable arm. An arm-receiving-side of the manual controller unit may be fixedly attached to the second-end of the adjustable arm. The manual controller unit may comprise a plurality of camera-operating-buttons for manually controlling the micro-camera located at a tip of the extendable wand. A camera-side of the manual controller unit may be fixedly mounted to a proximal-receiving end of the extendable wand.

The camera-housing may be located on a distal-recording end of the extendable wand. The camera-housing may comprise a camera-panner enabling the micro-camera to pan left, pan right, pan up, or pan down. Further, an extension of the extendable wand may comprise a zoom in function, and a retraction of the extendable wand may comprise a zoom out function. The user may be able to execute a camera-movement verbal command by vocalizing the camera-movement verbal command aloud into the microphone. The camera-movement verbal command may comprise the zoom in function and alternatively the zoom out function by causing the extendable wand to extend and alternatively retract in the hands-free manner accordingly. Further, the user is able to speak aloud the camera-movement verbal command for panning the micro-camera left, right, up, and down via the camera panner.

In the preferred embodiment of the present invention, the micro-camera is in communication with a monitor, and the micro-camera may be fittable into a 5 mm trocar device. The 5 mm trocar device may then be insertable into an abdomen of the patient during the surgical procedure for providing the user with an optimal vantage angle of the patient's abdomen during surgery.

The voice-activated hands-free camera holder system may be useful for enabling a user performing a surgical procedure on a patient to manipulate the micro-camera in a hands-free manner by speaking aloud a camera-movement verbal command into the microphone of the voice-activation assembly and alternatively enabling the user to manipulate the micro-camera manually via the plurality of camera-operating-buttons of the manual controller unit and having an image displayed on the monitor for enabling use of both hands of the user during the surgical procedure.

The voice-activated hands-free camera holder system may comprise a kit which may include the supporting bar, the voice-activation assembly, the adjustable arm, the manual controller unit, the extendable wand comprising the camera-housing for retaining the micro-camera, and a set of user instructions.

A method of using a voice-activated hands-free camera holder system may comprise the steps of installing the supporting bar to a patient operating system, activating the voice-activation assembly, positioning the adjustable arm, recording the surgical procedure, and viewing a user-preferred viewing angle of the surgical procedure on the monitor for display in real time. The method may further comprise an optional step of adjusting manually the extendable wand comprising the micro-camera via the manual controller unit.

The present invention holds significant improvements and serves as a voice-activated hands-free camera holder system. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, voice-activated hands-free camera holder systems, constructed and operative according to the teachings of the present invention.

The various embodiments of the present invention will hereinafter be described in conjunction with the appended drawings, wherein like designations denote like elements.

DETAILED DESCRIPTION

As discussed above, embodiments of the present invention relate to a hands-free camera holder and more particularly to a voice-activated hands-free camera holder system as used to improve a surgeon's ability to perform a surgical procedure by issuing vocal commands to manipulate a micro-camera that is synced to deliver a live feed from near the surgical area while having both hands available during the procedure.

Generally speaking, voice-activated hands-free camera holder systems 100 (AKA "Clara Cam") may comprise a voice-activated, hands-free camera holder for use during a surgical procedure. The invention may essentially comprise a metal pole supporting a telescoping arm that comprises a voice-activated, robotic box, two attachment points, and a series of coils that may extend to change the zoom and pan of the footage. The system may be constructed from stainless steel or another metal that may withstand the sterilization process. There may be a clamp that adheres to an operating table or other designated area. The clamp may be tightened into place by means of the supporting pole, which may extend from the clamp and reach an appropriate height to stand above a patient on the operating table. The top of the post may comprise a hole where the voice box and the arm of the device may be attached. This attachment point may comprise a ball and socket design to allow for easy adjustment of the angle.

The first portion of the arm may comprise the voice box, which may further comprise a microphone area on the top. The user, such as a surgeon, may speak into this area to control the movement of the camera head. The voice box may have a cord that plugs into a power outlet. There may be a flexible coil attached to the voice box. This coil may hold up the camera in a designated position. The flexible coil may also be attached to a camera control panel.

The control panel may comprise buttons on the surface to enable manual control of the device in situations where the surgeon may prefer not to use voice activation. The control buttons may comprise options to zoom in and out, as well as buttons for upward and downward movement. There may be a narrow, telescoping arm that extends from the control panel and features a small, high quality camera at an opposite end. The camera may resemble a snake head in its design. In one embodiment, the camera may fit into a 5 mm trocar device, which may then be inserted into a patient's abdomen. The design may allow for attachment to the operation bed at various angles.

The system may be connected to a viewing screen where the footage from the camera may be displayed. Further, the height of the device may be adjustable from about 16" to 32", and the length may adjust from about 4" to 24". The diameter of the design may be about 1.25" in preferred embodiments.

Figure 1:
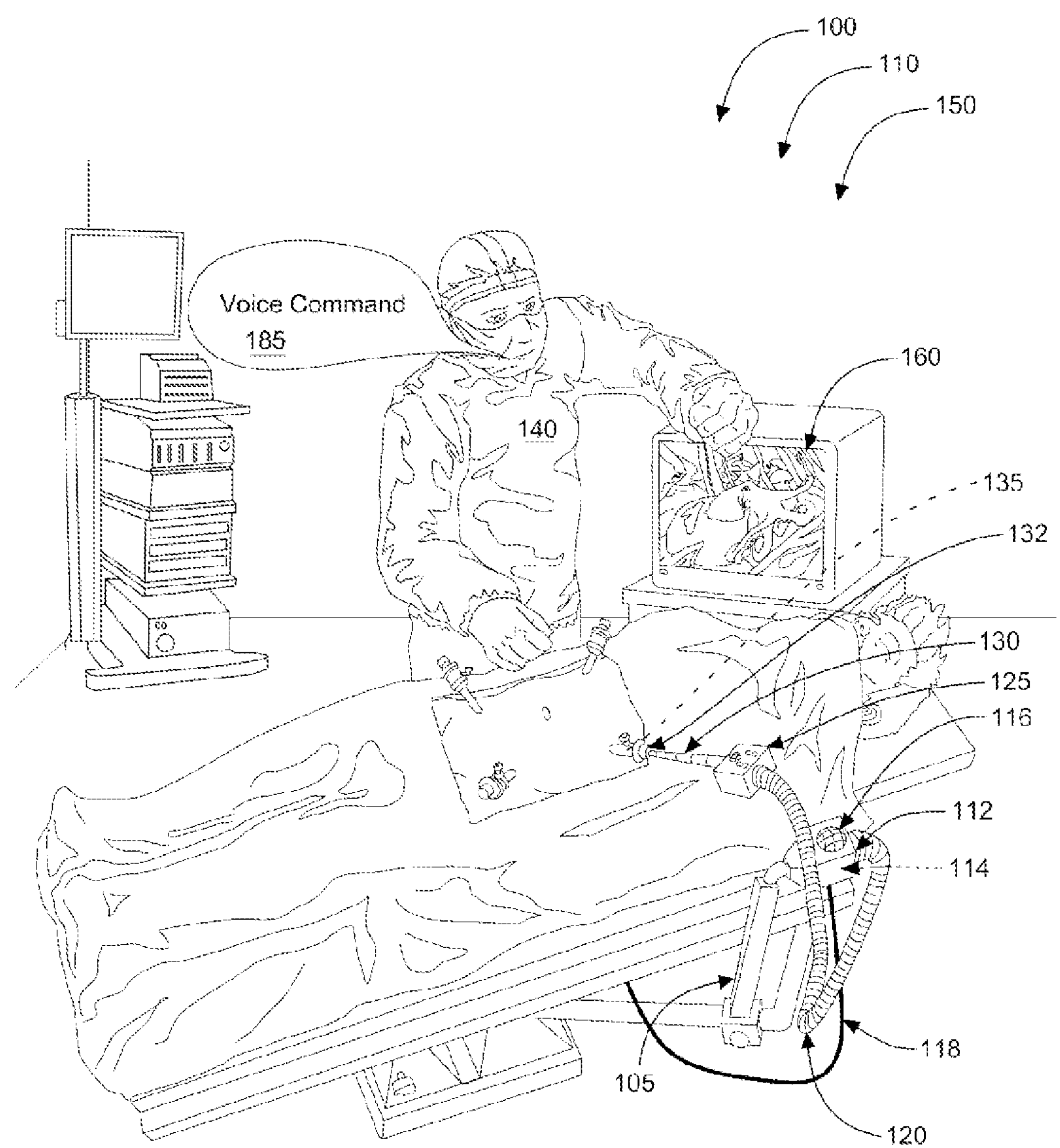
FIG. 1 shows a perspective view illustrating a voice-activated hands-free camera holder system during an 'in-use' condition showing a user-surgeon speaking a vocal command to adjust a micro-camera during a surgical procedure according to an embodiment of the present invention.

Referring to the drawings by numeral of reference, FIG. 1 shows a perspective view of voice-activated hands-free camera holder systems 100 during 'in-use' condition 150 according to an embodiment of the present invention. As shown, user 140 (such as a surgeon) may speak camera-movement verbal command(s) 185 to adjust micro-camera 135 while performing a surgical procedure. In such a manner, user 140 may manipulate micro-camera 135 in a hands-free manner allowing both hands of user 140 to be available during a surgical procedure. As shown, micro-camera 135 may transmit an image in real-time to monitor 160 which may comprise a display monitor for displaying the image as captured by micro-camera 135. For example, user 140 may adjust and view the image on monitor 160 using camera-movement verbal command(s) 185 while performing a surgical procedure, such as a laporoscopic surgical procedure, to perform the procedure having an optimal vantage point.

In still referring to FIG. 1, voice-activated hands-free camera holder systems 100 may comprise supporting bar 105, voice-activation assembly 110 and extendable wand 130. As shown, supporting bar 105 may comprise clamp 210 useful for attaching voice-activated hands-free camera holder systems 100 to a patient operating station, such as a hospital station or bed. Supporting bar 105 may be manufactured of sterilized stainless steel to withstand sterilization process.

In continuing to refer to FIG. 1, voice-activation assembly 110 is shown comprising voice-activation housing 112, voice-activation processor 114, microphone 116, power source 118, adjustable arm 120, and manual controller unit 125. Voice-activation housing 112, voice-activation processor 114, microphone 116, and power source 118 comprise in functional combination voice-activation assembly 110. As may be seen, voice-activation housing 112 may comprise a box-like enclosure having a first-side, second-side, top-side, and bottom-side. Voice-activation processor 114, microphone 116, and power source 118 may be fixedly mounted within voice-activation housing 112. Voice-activation processor 114, microphone 116, and power source 118 may be in electrical communication. It should be noted that voice-activation processor 114 operates voice-activation assembly 110 when activated and verbally (or manually) manipulated by user 140. Extendable wand 130 may comprise camera-housing 132 for retaining micro-camera 135. Voice-activated hands-free camera holder systems 100 may comprise in functional combination supporting bar 105, voice-activation assembly 110 and extendable wand 130.

Figure 2:
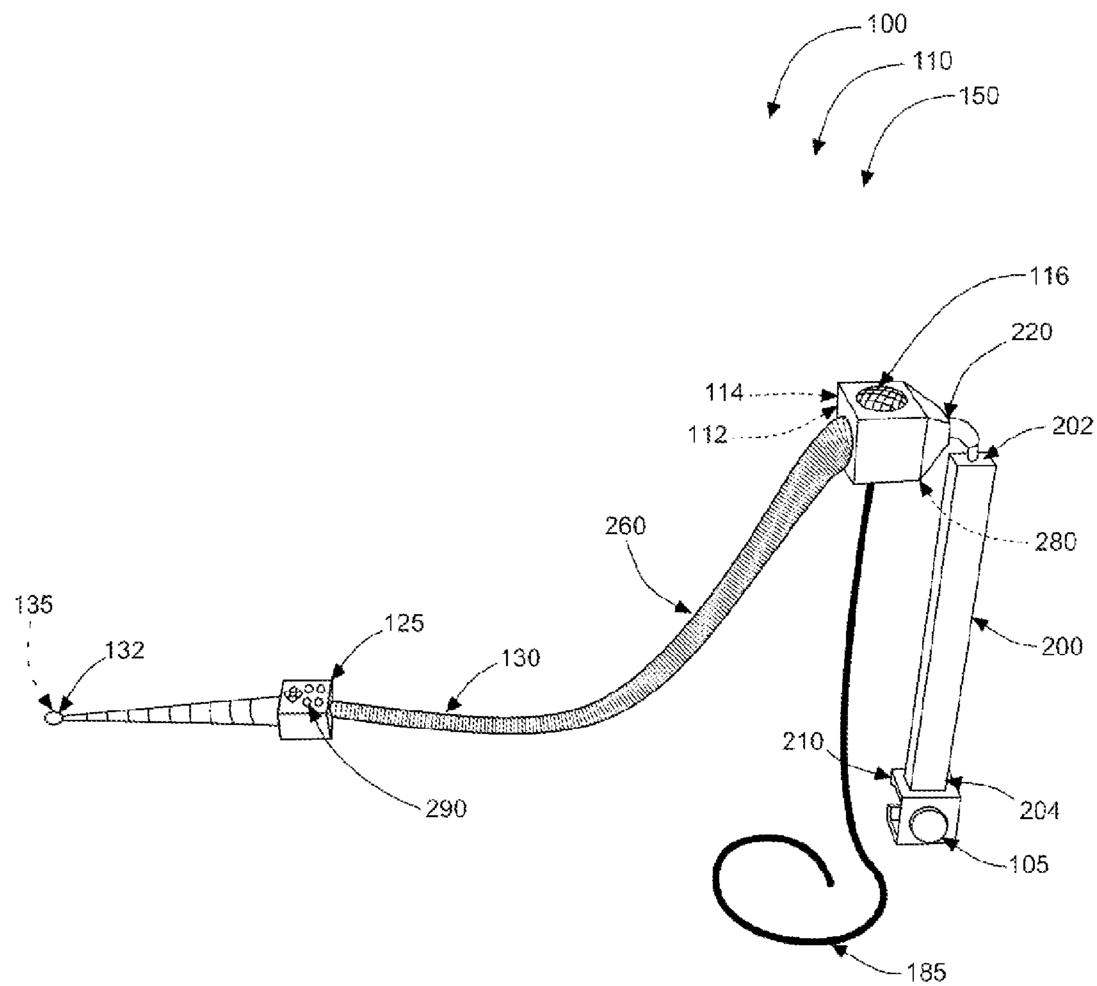
FIG. 2 is a perspective view illustrating a perspective view of the voice-activated hands-free camera holder system comprising a supporting bar, a voice-activation assembly, an adjustable arm, a manual controller unit, and an extendable wand comprising a camera-housing for retaining a micro-camera according to an embodiment of the present invention of FIG. 1.

Referring now to FIG. 2 showing a perspective view of voice-activated hands-free camera holder system 100 comprising supporting bar 105, voice-activation assembly 110, adjustable arm 120, manual controller unit 125, and extendable wand 130 comprising camera-housing 132 for retaining micro-camera 135 according to an embodiment of the present invention of FIG. 1. As shown, a top-side of voice-activation housing 112 may comprise microphone 116 comprising acoustic-to-electric transducer 280 useful to cause voice-activation assembly 110 to be verbally manipulated by user 140. Adjustable arm 120 comprises elongated flexible member 260 having a first-end and a second-end. A second-side of voice-activation housing 112 may comprise an opening for fixedly retaining the first-end of adjustable arm 120. An arm-receiving-side of manual controller unit 125 may be fixedly attached to the second-end of adjustable arm 120.

In continuing to refer to FIG. 2, voice-activation assembly 110 may be powered by power source 118 comprising a power cable connectable to an external power supplier. In an alternative embodiment, power source 118 may comprise at least one battery. Voice-activation assembly connecting point 220 may be rotatably-connected to first-side of voice-activation housing 112 via ball-and-socket joint 410.

Figure 3:
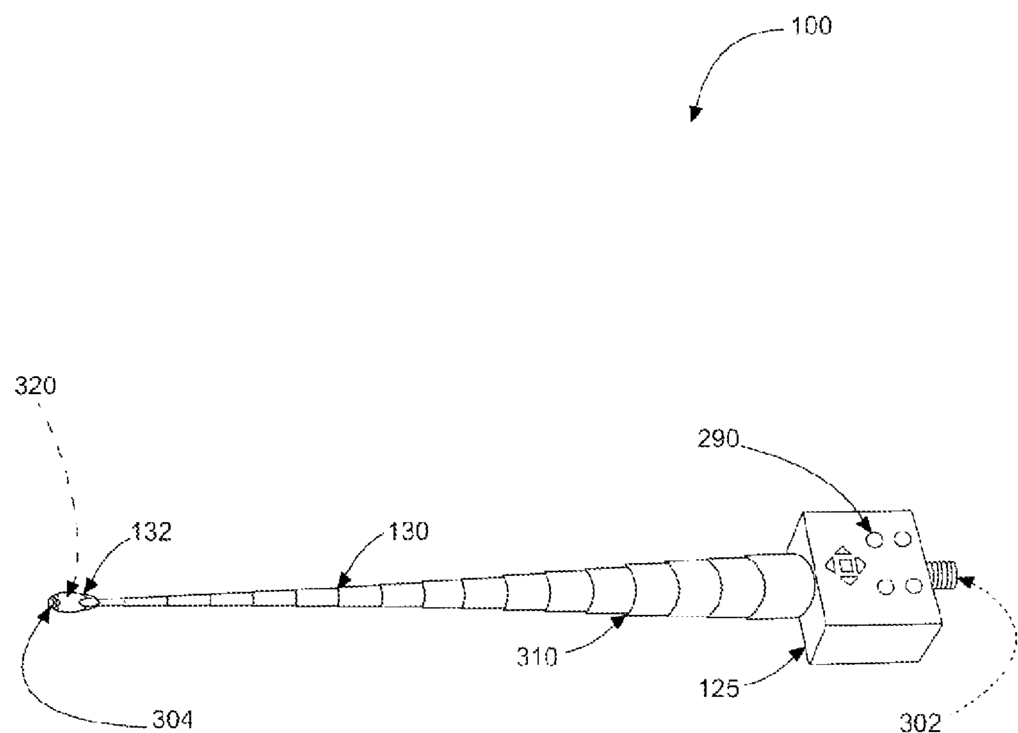
FIG. 3 is a perspective view illustrating a perspective view of the extendable wand comprising a plurality of telescopic-coils according to an embodiment of the present invention of FIG. 1.

Referring now to FIG. 3 showing a perspective view of extendable wand 130 comprising plurality of telescopic-coils 310 according to an embodiment of the present invention of FIG. 1. Plurality of telescopic-coils 310 may be structured and arranged in a stack relationship such that they may enable extendable wand 130 comprising camera-housing 132 and retaining micro-camera 135 to extend and retract as needed.

In continuing to refer to FIG. 3, manual controller unit 125 may comprise plurality of camera-operating-buttons 290 for manually controlling micro-camera 135 on extendable wand 130. During 'in-use' condition 150 a camera-side of manual controller unit 125 may be fixedly mounted to proximal-receiving end 302 of extendable wand 130. As may be seen, camera-housing 132 may be located on distal-recording end 304 of extendable wand 130, and micro-camera 135 may be in remote communication with monitor 160 for display in real time.

In continuing to refer to FIG. 3, voice-activated hands-free camera holder system 100 may comprise camera-panner 320. It may be appreciated that camera-panner 320 may enable micro-camera 135 to pan left, pan right, pan up, or pan down verbally via camera-movement verbal command 185 or manually via manual controller unit 125. Further, camera-movement verbal command 185 may comprise a zoom in function and alternatively a zoom out function useful for causing extendable wand 130 to extend outward and alternatively to retract inward while both hands of user 140 remain free.

As may be appreciated, voice-activated hands-free camera holder systems 100 may be useful for enabling user 140 performing a surgical procedure on a patient to manipulate micro-camera 135 in a hands-free manner by speaking aloud camera-movement verbal command 185 into microphone 116 of voice-activation assembly 110 and alternatively enabling user 140 to manipulate micro-camera 135 manually via plurality of camera-operating-buttons 290 of manual controller unit 125 and having the image displayed on monitor 160 for enabling use of both hands of user 140 during a surgical procedure.

Figure 4:
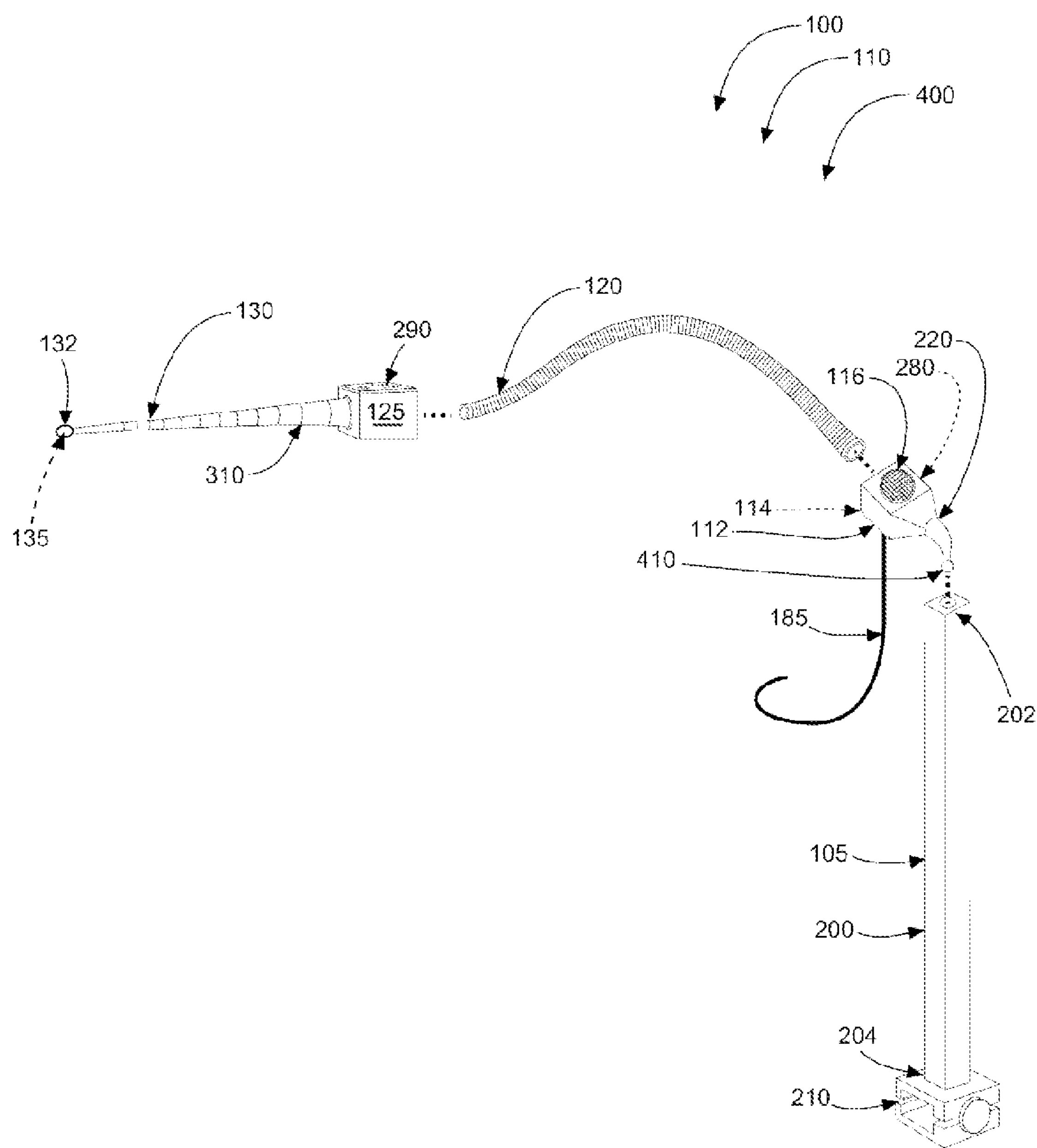
FIG. 4 is a perspective view illustrating an exploded view of the voice-activated hands-free camera holder system according to an embodiment of the present invention of FIG. 1.

Referring now to FIG. 4 showing exploded view 400 of voice-activated hands-free camera holder systems 100 according to an embodiment of the present invention of FIGS. 1-3. As shown, voice-activated hands-free camera holder systems 100 may comprise supporting bar 105 having clamp 210 for securing supporting bar 105 to the operating station. Supporting bar 105 may comprise rectangular member 200 having proximal end 202 and distal end 204. As shown, distal end 204 of rectangular member 200 may comprise clamp 210 and proximal end 202 of rectangular member 200 may comprise voice-activation assembly connecting point 220 for connecting voice-activation housing 112 of voice-activation assembly 110 to supporting bar 105. Supporting bar 105 may be adjustably-connected to voice-activation housing 112 of voice-activation assembly 110, which may be connected to adjustable arm 120 via ball-and-socket joint 410. Further, adjustable arm 120 may be attached to extendable wand 130 comprising camera-housing 132 and retaining micro-camera 135.

In one embodiment of the present invention, clamp 210 may comprise a C-clamp. The C-clamp may be useful for non-movably attaching supporting bar 105 to rail of the patient operating station and enabling supporting bar 105 to adjust vertically approximately 6-8" allowing user 140 to adjust supporting bar 105 to a user-preferred height. Plurality of telescopic-coils 310 may enable extendable wand 130 to extend and retract.

In one embodiment of the present invention, voice-activated hands-free camera holder systems 100 may work in combination with micro-camera 135 that is fittable into a 5 mm trocar device, such that the trocar device may be insertable into an abdomen of patient during a surgical procedure.

In another embodiment of the present invention, power source 118 of voice-activated hands-free camera holder systems 100 may comprise a battery that is rechargeable.

In another embodiment of the present invention, voice-activated hands-free camera holder systems 100 assembly may comprise a wireless receiver (for example, BLUETOOTH®) such that the wireless receiver may enable micro-camera 135 to be controlled by a mobile communication device having a wireless internet connection.

In an embodiment of the present invention, voice-activated hands-free camera holder systems 100 may comprise a kit. The kit may comprise supporting bar 105, voice-activation assembly 110, adjustable arm 120, manual controller unit 125, extendable wand 130 comprising camera-housing 132 for retaining micro-camera 135, and a set of user instructions. The kit has instructions such that functional relationships are detailed in relation to the structure of the invention (such that the invention can be used, maintained, or the like in a preferred manner). Voice-activated hands-free camera holder systems 100 may be manufactured and provided for sale in a wide variety of sizes and shapes for a wide assortment of applications. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized parts, different color combinations, parts may be sold separately, etc., may be sufficient.

Figure 5:
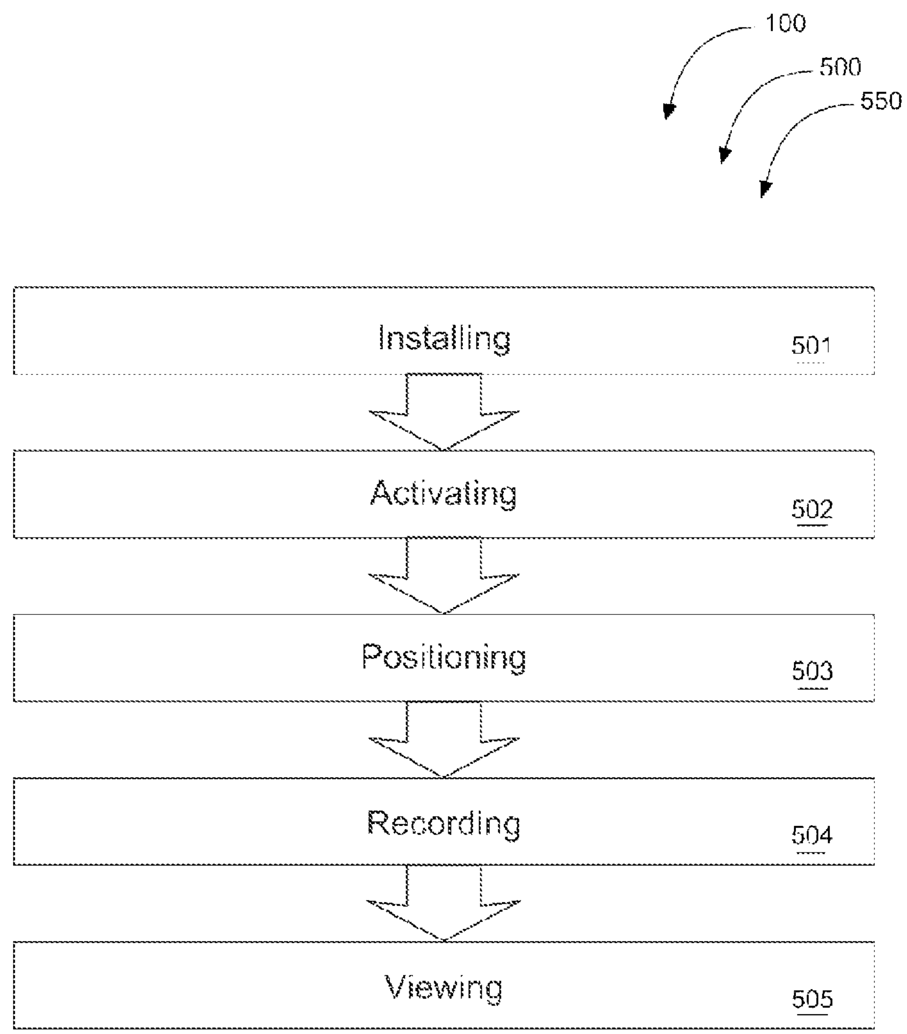
FIG. 5 is a flowchart illustrating a method of use for the voice-activated hands-free camera holder system according to an embodiment of the present invention of FIGS. 1-4.

Referring now to FIG. 5, showing flowchart 550 illustrating method of use 500 for voice-activated hands-free camera holder systems 100 according to an embodiment of the present invention of FIGS. 1-4. As shown, method of use 500 may comprise the steps of: step one 501, installing supporting bar 105 to a patient operating station; step two 502, activating voice-activation assembly 110; step three 503, positioning adjustable arm 120; step four 504, recording a surgical procedure; and step five 505, viewing a user-preferred viewing angle of the surgical procedure on monitor 160 for display in real time of the user-preferred viewing angle.

Method of use 500 may further comprise the step of step six 506 adjusting manually extendable wand 130 comprising micro-camera 135 via manual controller unit 125. It should be noted that step six 506 is an optional step and may not be implemented in all cases. Optional steps of method 500 are illustrated using dotted lines in FIG. 5 so as to distinguish them from the other steps of method 500.

It should be noted that the steps described in the method of use can be carried out in many different orders according to user preference. The use of "step of" should not be interpreted as "step for", in the claims herein and is not intended to invoke the provisions of 35 U.S.C. §112, ¶6. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A voice-activated hands-free camera holder system comprising:

a supporting bar;

a voice-activation assembly comprising;

a voice-activation housing;

at least one voice-activation processor;

at least one microphone; and a power source;

an adjustable arm;

a manual controller unit; and an extendable wand comprising at least one camera-housing for retaining at least one micro-camera;

wherein said supporting bar, said voice-activation assembly, said adjustable arm, said manual controller unit, and said extendable wand comprises in functional combination said voice-activated hands-free camera holder system;

wherein said supporting bar comprises a rectangular member having a proximal end and a distal end;

wherein said distal end of said rectangular member comprises at least one clamp;

wherein said proximal end of said rectangular member comprises a voice-activation assembly connecting point for connecting said voice-activation housing of said voice-activation assembly to said supporting bar;

wherein said voice-activation housing, said at least one voice-activation processor, said at least one microphone, and said power source comprise in functional combination said voice-activation assembly;

wherein said voice-activation housing comprises a box-like enclosure having a first-side, a second-side, a top-side, and a bottom-side;

wherein said at least one voice-activation processor, said at least one microphone, and said power source are fixedly mounted within said voice-activation housing;

wherein said at least one voice-activation processor, said at least one microphone, and said power source are in electrical communication;

wherein said at least one voice-activation processor operates said voice-activation assembly when activated and verbally manipulated by a user;

wherein said voice-activation assembly is powered by said power source, said power source comprising a power cable connectable to at least one external power supplier;

wherein said voice-activation assembly connecting point is rotatably-connected to said first-side of said voice-activation housing via a ball-and-socket joint;

wherein said top-side of said voice-activation housing comprises said microphone comprising an acoustic-to-electric transducer useful to cause said voice-activation assembly to be verbally manipulated by said user;

wherein said adjustable arm comprises an elongated flexible member having a first-end and a second-end;

wherein said second-side of said voice-activation housing comprises an adjustable arm opening for fixedly retaining said first-end of said adjustable arm;

wherein an arm-receiving-side of said manual controller unit is fixedly attached to said second-end of said adjustable arm;

wherein said manual controller unit comprises a plurality of camera-operating-buttons for manually controlling said at least one micro-camera of said extendable wand;

wherein a camera-side of said manual controller unit is fixedly mounted to a proximal-receiving end of said extendable wand;

wherein said at least one camera-housing is located on a distal-recording end of said extendable wand;

wherein said at least one micro-camera is in communication with at least one monitor for display in real time; and wherein said voice-activated hands-free camera holder system is useful for enabling said user performing a surgical procedure on a patient to manipulate said at least one micro-camera in a hands-free manner by speaking aloud at least one camera-movement verbal command into said at least one microphone of said voice-activation assembly and alternatively enabling said user to manipulate said at least one micro-camera manually via said plurality of camera-operating-buttons of said manual controller unit and having an image displayed on said monitor for enabling use of both hands of said user during said surgical procedure.

2. The voice-activated hands-free camera holder system of claim 1 wherein said extendable wand, said adjustable arm, and said supporting bar are manufactured of sterilized stainless steel to withstand at least one sterilization process.

3. The voice-activated hands-free camera holder system of claim 2 wherein said at least one clamp comprises a C-clamp.

4. The voice-activated hands-free camera holder system of claim 3 wherein said C-clamp is useful for non-movably attaching said support bar to at least one rail of a patient operating station.

5. The voice-activated hands-free camera holder system of claim 4 wherein said C-clamp enables said supporting bar to adjust vertically approximately 6-8" for allowing said user to adjust said supporting bar to a user-preferred height.

6. The voice-activated hands-free camera holder system of claim 5 wherein said extendable wand comprises a plurality of telescopic-coils which enable said extendable wand to extend and retract.

7. The voice-activated hands-free camera holder system of claim 6 wherein said at least one camera-housing comprises a camera-panner enabling said at least one micro-camera to pan left, pan right, pan up, or pan down.

8. The voice-activated hands-free camera holder system of claim 7 wherein an extension of said extendable wand comprises a zoom in function.

9. The voice-activated hands-free camera holder system of claim 8 wherein a retraction of said extendable wand comprises a zoom out function.

10. The voice-activated hands-free camera holder system of claim 9 wherein said at least one camera-movement verbal command comprises said zoom in function and alternatively said zoom out function for causing said extendable wand to extend and alternatively retract in said hands-free manner accordingly.

11. The voice-activated hands-free camera holder system of claim 10 wherein said user is able to speak aloud said at least one camera-movement verbal command for panning said at least one micro-camera left, right, up, and down via said camera panner.

12. The voice-activated hands-free camera holder system of claim 11 wherein said at least one micro-camera is fittable into a 5 mm trocar device.

13. The voice-activated hands-free camera holder system of claim 12 wherein said 5 mm trocar device is insertable into an abdomen of said patient during said surgical procedure.

14. The voice-activated hands-free camera holder system of claim 13 wherein said power source alternatively comprises a rechargeable battery.

15. The voice-activated hands-free camera holder system of claim 13 wherein said voice-activation assembly comprises a Bluetooth receiver.

16. The voice-activated hands-free camera holder system of claim 15 wherein said Bluetooth receiver enables said at least one micro-camera to be controlled by at least one mobile communication device comprising Bluetooth.

17. A voice-activated hands-free camera holder system comprising:

a supporting bar manufactured of sterilized stainless steel to withstand a sterilization process;

a voice-activation assembly comprising;

a voice-activation housing;

at least one voice-activation processor;

at least one microphone; and a power source;

an adjustable arm manufactured of sterilized stainless steel to withstand said sterilization process;

a manual controller unit; and an extendable wand manufactured of sterilized stainless steel to withstand said sterilization process, said extendable wand comprising at least one camera-housing for retaining at least one micro-camera, said extendable wand further comprising a plurality of telescopic-coils which enable said extendable wand to extend and retract;

wherein said supporting bar, said voice-activation assembly, said adjustable arm, said manual controller unit, and said extendable wand comprises in functional combination said voice-activated hands-free camera holder system;

wherein said supporting bar comprises a rectangular member having a proximal end and a distal end;

wherein said distal end of said rectangular member comprises at least one clamp, said clamp comprising a C-clamp, said C-clamp useful for non-movably attaching said support bar to at least one rail of a patient operating station, said C-clamp further enabling said supporting bar to adjust vertically approximately 6-8" for allowing said user to adjust said supporting bar to a user-preferred height;

wherein said proximal end of said rectangular member comprises a voice-activation assembly connecting point for connecting said voice-activation housing of said voice-activation assembly to said supporting bar;

wherein said voice-activation housing, said at least one voice-activation processor, said at least one microphone, and said power source comprise in functional combination said voice-activation assembly;

wherein said voice-activation housing comprises a box-like enclosure having a first-side, a second-side, a top-side, and a bottom-side;

wherein said at least one voice-activation processor, said at least one microphone, and said power source are fixedly mounted within said voice-activation housing;

wherein said at least one voice-activation processor, said at least one microphone, and said power source are in electrical communication;

wherein said at least one voice-activation processor operates said voice-activation assembly when activated and verbally manipulated by a user;

wherein said voice-activation assembly is powered by said power source, said power source comprising a power cable connectable to at least one external power supplier;

wherein said voice-activation assembly connecting point is rotatably-connected to said first-side of said voice-activation housing via a ball-and-socket joint;

wherein said top-side of said voice-activation housing comprises said microphone comprising an acoustic-to-electric transducer useful to cause said voice-activation assembly to be verbally manipulated by said user;

wherein said adjustable arm comprises an elongated flexible member having a first-end and a second-end;

wherein said second-side of said voice-activation housing comprises an adjustable arm opening for fixedly retaining said first-end of said adjustable arm;

wherein an arm-receiving-side of said manual controller unit is fixedly attached to said second-end of said adjustable arm;

wherein said manual controller unit comprises a plurality of camera-operating-buttons for manually controlling said at least one micro-camera of said extendable wand;

wherein a camera-side of said manual controller unit is fixedly mounted to a proximal-receiving end of said extendable wand;

wherein said at least one camera-housing is located on a distal-recording end of said extendable wand;

wherein said at least one camera-housing comprises a camera-panner enabling said at least one micro-camera to pan left, pan right, pan up, or pan down;

wherein an extension of said extendable wand comprises a zoom in function;

wherein a retraction of said extendable wand comprises a zoom out function;

wherein said user is able to execute at least one camera-movement verbal command by vocalizing said at least one camera-movement verbal command aloud into said microphone;

wherein said at least one camera-movement verbal command comprises said zoom in function and alternatively said zoom out function for causing said extendable wand to extend and alternatively retract in said hands-free manner accordingly;

wherein said user is able to speak aloud said at least one camera-movement verbal command for panning said at least one micro-camera left, right, up, and down via said camera panner;

wherein said at least one micro-camera is in communication with at least one monitor;

wherein said at least one micro-camera is fittable into a 5 mm trocar device;

wherein said 5 mm trocar device is insertable into an abdomen of said patient during said surgical procedure; and wherein said voice-activated hands-free camera holder system is useful for enabling a user performing a surgical procedure on a patient to manipulate said at least one micro-camera in a hands-free manner by speaking aloud at least one camera-movement verbal command into said at least one microphone of said voice-activation assembly and alternatively enabling said user to manipulate said at least one micro-camera manually via said plurality of camera-operating-buttons of said manual controller unit and having an image displayed on said monitor for enabling use of both hands of said user during said surgical procedure.

18. The voice-activated hands-free camera holder system of claim 17 further comprising a kit including:

said supporting bar;

said voice-activation assembly;

said adjustable arm;

said manual controller unit;

said extendable wand comprising said at least one camera-housing for retaining said at least one micro-camera; and a set of user instructions.

19. A method of providing and using a voice-activated hands-free camera holder system comprising the steps of:

providing a voice-activated hands-free camera holder system comprising:

a supporting bar;

a voice-activation assembly comprising;

a voice-activation housing;

at least one voice-activation processor;

at least one microphone; and a power source;

an adjustable arm;

a manual controller unit; and an extendable wand comprising at least one camera-housing for retaining at least one micro-camera;

wherein said supporting bar, said voice-activation assembly, said adjustable arm, said manual controller unit, and said extendable wand comprises in functional combination said voice-activated hands-free camera holder system;

wherein said supporting bar comprises a rectangular member having a proximal end and a distal end;

wherein said distal end of said rectangular member comprises at least one clamp;

wherein said proximal end of said rectangular member comprises a voice-activation assembly connecting point for connecting said voice-activation housing of said voice-activation assembly to said supporting bar;

wherein said voice-activation housing, said at least one voice-activation processor, said at least one microphone, and said power source comprise in functional combination said voice-activation assembly;

wherein said voice-activation housing comprises a box-like enclosure having a first-side, a second-side, a top-side, and a bottom-side;

wherein said at least one voice-activation processor, said at least one microphone, and said power source are fixedly mounted within said voice-activation housing;

wherein said at least one voice-activation processor, said at least one microphone, and said power source are in electrical communication;

wherein said at least one voice-activation processor operates said voice-activation assembly when activated and verbally manipulated by a user;

wherein said voice-activation assembly is powered by said power source, said power source comprising a power cable connectable to at least one external power supplier;

wherein said voice-activation assembly connecting point is rotatably-connected to said first-side of said voice-activation housing via a ball-and-socket joint;

wherein said top-side of said voice-activation housing comprises said microphone comprising an acoustic-to-electric transducer useful to cause said voice-activation assembly to be verbally manipulated by said user;

wherein said adjustable arm comprises an elongated flexible member having a first-end and a second-end;

wherein said second-side of said voice-activation housing comprises an adjustable arm opening for fixedly retaining said first-end of said adjustable arm;

wherein an arm-receiving-side of said manual controller unit is fixedly attached to said second-end of said adjustable arm;

wherein said manual controller unit comprises a plurality of camera-operating-buttons for manually controlling said at least one micro-camera of said extendable wand;

wherein a camera-side of said manual controller unit is fixedly mounted to a proximal-receiving end of said extendable wand;

wherein said at least one camera-housing is located on a distal-recording end of said extendable wand;

wherein said at least one micro-camera is in communication with at least one monitor for display in real time; and wherein said voice-activated hands-free camera holder system is useful for enabling said user performing a surgical procedure on a patient to manipulate said at least one micro-camera in a hands-free manner by speaking aloud at least one camera-movement verbal command into said at least one microphone of said voice-activation assembly and alternatively enabling said user to manipulate said at least one micro-camera manually via said plurality of camera-operating-buttons of said manual controller unit and having an image displayed on said monitor for enabling use of both hands of said user during said surgical procedure;

installing said supporting bar to a patient operating station;

activating said voice-activation assembly;

positioning said adjustable arm;

recording said surgical procedure; and viewing a user-preferred viewing angle of said surgical procedure on at least one said monitor for display in real time.

20. The method of claim 19 further comprising the step of:

adjusting manually said extendable wand comprising at least one said micro-camera via said manual controller unit.

* * * * *